United States Patent
Sicken et al.

(10) Patent No.: US 7,129,320 B2
(45) Date of Patent: Oct. 31, 2006

(54) MODIFIED POLYETHYLENEPHOSPHINIC ACIDS AND THEIR SALTS

(75) Inventors: Martin Sicken, Cologne (DE); Werner Krause, Huerth (DE); Norbert Weferling, Huerth (DE); Hans-Peter Schmitz, Bruehl (DE)

(73) Assignee: Clariant GmbH, Frankfurt (DE)

( * ) Notice: Subject to any disclaimer, the term of this patent is extended or adjusted under 35 U.S.C. 154(b) by 4 days.

(21) Appl. No.: 10/793,315

(22) Filed: Mar. 4, 2004

(65) Prior Publication Data

US 2004/0176580 A1 Sep. 9, 2004

(30) Foreign Application Priority Data

Mar. 4, 2003 (DE) ................ 103 09 570

(51) Int. Cl.
*C08G 79/02* (2006.01)
*C08F 30/02* (2006.01)

(52) U.S. Cl. ............... 528/398; 528/489; 528/497; 525/538; 562/20; 526/274; 526/275

(58) Field of Classification Search ........... 528/398, 528/489, 497; 525/538; 562/20; 526/274, 526/275
See application file for complete search history.

(56) References Cited

U.S. PATENT DOCUMENTS

| | | | |
|---|---|---|---|
| 6,300,516 B1 | 10/2001 | Weferling et al. | |
| 6,329,544 B1 | 12/2001 | Weferling et al. | |
| 6,359,171 B1 | 3/2002 | Weferling et al. | |
| 6,388,125 B1 | 5/2002 | Schmitz et al. | |
| 6,569,974 B1 | 5/2003 | Sicken et al. | |
| 6,583,315 B1 | 6/2003 | Sicken et al. | |
| 6,600,067 B1 | 7/2003 | Sicken et al. | |
| 6,600,068 B1 | 7/2003 | Sicken et al. | |
| 6,727,335 B1 | 4/2004 | Sicken et al. | |
| 2003/0216533 A1 | 11/2003 | Sicken et al. | |

FOREIGN PATENT DOCUMENTS

| | | |
|---|---|---|
| DE | 19851618 | 6/1999 |
| DE | 19912920 | 9/2000 |
| WO | WO 01/57050 | 8/2001 |

OTHER PUBLICATIONS

Sicken et al, Polymeric phosphinic acids and their salts, 2000, Chem Abstract 133: 267252.*
Maier, "Synthesis and Properties of Bis(phosphonylethyl)phosphinates and the corresponding Acid," Phosphorus, vol. 1, pp. 105-109 (1971).
Mastalerz, "Synthesis of some Ethylene-(P, P'-Dialkyl)-Diphosphinic Acids as New Potential Antimetabolites of Sucvcinic Acid, "Roczniki Chenmii Ann. Soc. Chim. Polonorum 38, pp. 61-64 (1964).
Block, "Polymeric Metal Phosphinates" Inorganic Macromolecules Reviews, pp. 115-125 (1970).
Nifant'ev et al., "Reactions of Acetylenes with Hypophosphorous and Phosphonous Acids" Zh. Obshch. Kim. 56(4), pp. 773-781 (1986) [English Translation].

* cited by examiner

*Primary Examiner*—Duc Truong
(74) *Attorney, Agent, or Firm*—Anthony A. Bisulca

(57) ABSTRACT

The invention relates to polymeric phosphinic acids and their salts of the formula (I)

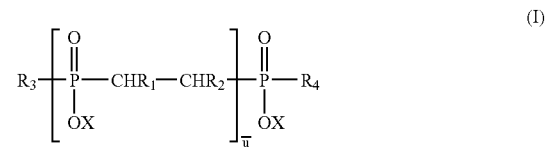

where
X is hydrogen or 1/m of a metal of valency m, or is a protonated nitrogen base,
$R_1$ and $R_2$ are identical or different and are hydrogen, a carboxy group, a carboxylic acid derivative, an unsubstituted or substituted alkyl group having from 1 to 10 carbon atoms, phenyl, benzyl, or alkyl-substituted aromatic systems, $R_3$ and $R_4$ may be identical or different and are an unsubstituted or substituted alkyl group having from 2 to 20 carbon atoms, or are OX, with the above meaning for X, and $\bar{u}$ is the average number of monomer units.

The invention further relates to a process for preparing the above-mentioned compounds, and to their use.

14 Claims, No Drawings

MODIFIED POLYETHYLENEPHOSPHINIC ACIDS AND THEIR SALTS

The present invention relates to novel modified polymeric phosphinic acids and their salts, and also to a process for their preparation, and to their use.

Phosphinic acids and their salts can be prepared by various methods and are widely described in the literature. Most of the phosphinic acids known hitherto are monomeric, i.e. phosphinic acids which contain only one phosphinic acid group. Some diphosphinic acids and their salts are also known, e.g. ethane-1,2-diethylphosphinic acid (P. Mastalerz, Roczniki Chem. 38, 61 (1964)).

References to polymeric phosphinic acids are hitherto restricted to coordination polymers, where monomeric phosphinic acids function as bridging ligands for metal ions. B. P. Block, Inorg. Macromol. Rev., 1 (1970) 115–125 gives an overview of this product group, termed polymeric metal phosphinates.

The free-radical-initiated reaction of olefins with hypophosphorous acid is known, and leads to the corresponding monomeric phosphinic acids (DE-A-198 51 618).

The free-radical-initiated reaction of alkynes (acetylenes) with hypophosphorous acid has likewise been studied [Nifant'ev et al., Zh. Obshch. Khim. (1986), 56(4) pp. 773–781]; the reaction products obtained were merely mixtures of vinylphosphonous acids, divinylphosphinic acids, and diphosphonous acids.

"Genuine" polymeric phosphinic acids, i.e. those whose structure is based on covalent bonds and whose repeat units contain phosphinic acid groups, were first mentioned in DE 199 12 920 A1. That publication describes products of the formula (I)

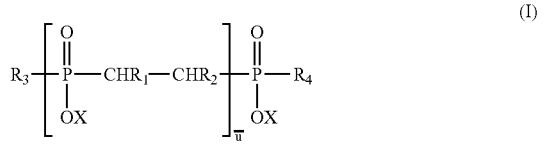

where X is a hydrogen atom or 1/m of a metal of valency m, $R_1$ and $R_2$ may be identical or different, and are hydrogen, a carboxy group, a carboxylic acid derivative, an unsubstituted or substituted alkyl group having from 1 to 10 carbon atoms, phenyl, benzyl, or alkyl-substituted aromatic systems, $R_3$ and $R_4$ may be identical or different, and are hydrogen or a vinyl group of the formula (VI)

$$-CR_1=CHR_2 \quad (VI)$$

with the meanings stated above for $R_1$ and $R_2$, and $\bar{u}$ means the average number of monomer units.

These polymeric products have the disadvantage that the end groups defined by $R_3$ and $R_4$ have only low chemical and thermal resistance, the result being that in the application proposed by way of example as flame retardant these products can undergo undesired side-reactions.

This applies especially to the products mentioned as particularly preferred, where $R_3$ and $R_4$=H (phosphonous acid end groups), these being capable under certain circumstances of liberating phosphorus products of lower oxidation states, e.g. substituted phosphines, via disproportionation. Phosphines are highly toxic and have extremely unpleasant odors.

It is an object of the invention, therefore, to provide polymeric phosphinic acids which do not have the above-mentioned disadvantages, and in particular have modified end groups.

The invention therefore provides polymeric phosphinic acids and their salts of the formula (I)

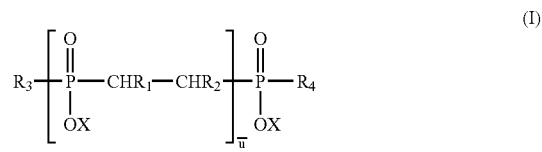

where X is hydrogen or 1/m of a metal of valency m, or is a protonated nitrogen base, $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatic systems, $R_3$ and $R_4$ may be identical or different and are an unsubstituted or substituted alkyl group having from 2 to 20 carbon atoms, or are OX, with the above meaning for X, and $\bar{u}$ is the average number of monomer units.

X is preferably a metal of groups IA, IIA, IIIA, IVA, VA, IIB, IVB, VIIB, VIIIB of the Periodic Table of the Elements, or is cerium.

The metal is preferably Li, Na, K, Mg, Ca, Sr, Ba, Al, Ge, Sn, Sb, Bi, Zn, Ti, Zr, Mn, Fe and/or Ce.

The metal is particularly preferably Na, Ca, Al and/or Zn.

A preferred meaning of X is H.

Another preferred meaning of X is the protonated forms of the nitrogen bases ammonia, melamine, triethanolamine. These protonated nitrogen bases are therefore in particular those of the formula $NH_4^+$, $C_3N_6H_7^+$, $(CH_3CHOH)NH^+$. These protonated nitrogen bases are also termed "amine-$H^+$" hereinafter.

A preferred meaning of $R_1$ and $R_2$, these being identical or different, is hydrogen or an unsubstituted or substituted alkyl group having from 1 to 10 carbon atoms.

Another preferred meaning of $R_1$ and $R_2$, these being identical or different, is hydrogen or an unsubstituted or substituted alkyl group having from 1 to 10 carbon atoms, where the substituents are one or more of the groups OH, CN, $NH_2$.

Another preferred meaning of $R_1$ and $R_2$, these being identical or different, is hydrogen or an alkyl group having from 1 to 4 carbon atoms and having substitution by one or two OH groups.

Another preferred meaning of $R_1$ and $R_2$, these being identical or different, is hydrogen or a carboxylic acid derivative.

Another preferred meaning of $R_1$ and $R_2$, these being identical or different, is hydrogen or a carboxylic acid derivative of the formula COOR, where R is an alkyl group having from 1 to 4 carbon atoms.

A preferred meaning of $R_3$ and $R_4$ is an unsubstituted or substituted alkyl group having from 1 to 10 carbon atoms.

Another preferred meaning of each of $R_3$ and $R_4$ is an ethyl, propyl, or butyl group.

Another preferred meaning of each of $R_3$ and $R_4$ is an OX group, with the meaning given above for X.

Another preferred meaning of each of $R_3$ and $R_4$ is an OH group.

The present invention in particular provides polymeric phosphinic acids and their salts of the formulae

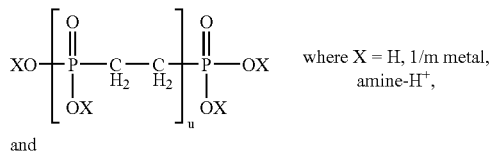

where X = H, 1/m metal, amine-H⁺, and

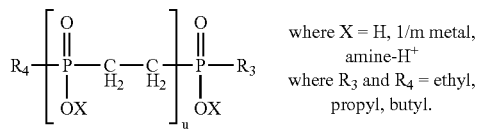

where X = H, 1/m metal, amine-H⁺
where $R_3$ and $R_4$ = ethyl, propyl, butyl.

The invention likewise provides a process for preparing polymeric phosphinic acids and their salts of the formula (I), which comprises first reacting hypophosphorous acid and/or its alkali metal salts with alkynes (acetylenes) of the formula (II),

where $R_1$ and $R_2$ are identical or different and are hydrogen, a carboxy group, a carboxylic acid derivative, an unsubstituted or substituted alkyl group having from 1 to 10 carbon atoms, phenyl, benzyl, or alkyl-substituted aromatic systems, to give products of the formula (I)

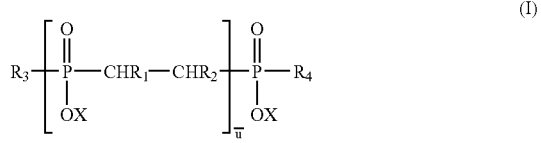

where $R_1$ and $R_2$ have the meaning given above,
$R_3$ and $R_4$ are hydrogen,
X is an alkali metal or hydrogen, and
ū indicates the average number of monomer units,
and then inverting the resultant phosphonous acid end groups ($R_3$ and $R_4$=H) to give phosphonic acid end groups ($R_3$ and $R_4$=OX) via oxidation, or to give phosphinic acid end groups ($R_3$ and $R_4$=alkyl) via alkylation, and then, where appropriate, further reacting the products (variation of X).

In a preferred method, alkali metal salts of hypophosphorous acid are reacted with alkynes (acetylenes) of the formula (II) as described above, the end groups are modified, and then the resultant alkali metal salts of the polymeric phosphinic acid are reacted with at least one metal compound of groups IA, IIA, IIIA, IVA, VA, IIB, IVB, VIIB, VIIIB of the Periodic Table of the Elements, or with a cerium compound, or with amines or amine salts. This process therefore includes the conversion of a first alkali metal salt of the polymeric phosphinic acid into another alkali metal salt of the polymeric phosphinic acid.

In another preferred procedure, hypophosphorous acid is reacted with alkynes (acetylenes) of the formula (II) as described above, the end groups are modified, and the resultant polymeric phosphinic acids are then reacted with at least one metal compound of groups IA, IIA, IIIA, IVA, VA, IIB, IVB, VIIB, VIIIB of the Periodic Table of the Elements, or with a cerium compound, or with amines or amine salts (the protonated nitrogen bases).

The metal compound is preferably a compound of Li, K, Na, Mg, Ca, Sr, Ba, Al, Ge, Sn, Sb, Bi, Zn, Ti, Zr, Mn, Fe, and/or Ce.

The amines are preferably melamine, ammonia, trialkylamines, or ethanolamines.

In a preferred method, alkali metal salts of hypophosphorous acid are reacted with alkynes (acetylenes) of the formula (II) as described above, the end groups are modified, and the resultant alkali metal salts of the polymeric phosphinic acid are reacted with an acid to give the polymeric phosphinic acid. The resultant polymeric phosphinic acid may then be subjected to one or more of the abovementioned processing steps.

There are therefore various ways of varying the variable X in formula (I), as set out above. By way of example, if the starting material subjected to the reaction above with alkynes (acetylenes) comprises the readily obtainable alkali metal salts of hypophosphorous acid, the corresponding polymeric alkali metal phosphinates are obtained, for example where X=Li, Na, or K in formula (I).

If the starting material used comprises hypophosphorous acid, the result is the free polyphosphinic acids, where X=H in formula (I). These acids may also be obtained by acidifying the alkali metal phosphinates.

Familiar precipitation and salt-exchange processes may be used to obtain polyphosphinic acid salts of numerous metals, e.g. of the alkaline earth metals, of the metals of main group II–V, or else of the transition group metals, or else of amines, from the alkali metal salts of the polyphosphinic acids, or from the free polyphosphinic acids.

It is preferable to use from 0.6 to 1.5 mol of ethyne (acetylene) of the formula (II) per mole of hypophosphorous acid or of its alkali metal salt.

The reaction preferably takes place in the presence of a free-radical initiator.

The free-radical initiators are preferably metered in continuously during the reaction.

In a preferred method, the free-radical initiators are metered in continuously in the form of a solution in the olefin during the reaction.

In another preferred method, the free-radical initiators are metered in continuously in the form of a solution in the solvent used during the reaction.

Free-radical initiators whose use is preferred are azo compounds.

The azo compounds used preferably comprise cationic and/or non-cationic azo compounds.

The cationic azo compounds used preferably comprise 2,2'-azobis(2-amidinopropane)dihydrochloride or 2,2'-azobis(N,N'-dimethyleneisobutyramidine)dihydrochloride.

The non-cationic azo compounds used preferably comprise azobis(isobutyronitrile), 4,4'-azobis(4-cyanopentanoic acid), or 2,2'-azobis(2-methylbutyronitrile).

Other free-radical initiators whose use is preferred are peroxidic inorganic and/or peroxidic organic free-radical initiators.

The peroxidic inorganic free-radical initiators preferably used are hydrogen peroxide, ammonium peroxodisulfate, sodium peroxodisulfate and/or potassium peroxodisulfate.

The peroxidic organic free-radical initiators preferably used comprise dibenzoyl peroxide, di-tert-butyl peroxide and/or peracetic acid.

The reaction preferably takes place in a polar solvent.
The polar solvent used preferably comprises water or acetic acid.

The reaction preferably takes place at a temperature of from 20 to 180° C.

The reaction particularly preferably takes place at a temperature of from 80 to 120° C.

The reaction preferably takes place in a pressure reactor. This applies in particular if the boiling point of the alkynes (acetylenes) is below the reaction temperature.

In another preferred embodiment of the invention, the process is carried out at atmospheric pressure.

The starting material used preferably comprises hypophosphorous acid and/or alkali metal salts of hypophosphorous acid.

It is particularly preferable to use sodium hypophosphite.

The alkynes (acetylenes) used may either be unsubstituted ethyne (acetylene) itself, where $R_1$ and $R_2$=H in formula (II), monosubstituted derivatives, where $R_1$=H;

$R_2 \neq H$ in formula (II), or else disubstituted alkynes (acetylenes), where $R_1$ and $R_2 \neq H$ in formula (II).

Examples of suitable alkynes (acetylenes) are ethyne, phenylacetylene, diphenylacetylene, propyne, 1-butyne, 2-butyne, 1-phenylbutyne, 1-pentyne, 2-pentyne, 1-phenyl-1-pentyne, 1-hexyne, 2-hexyne, 3-hexyne, 1-phenyl-1-hexyne, 1-heptyne, 1-octyne, 4-octyne, 1-nonyne, 1-decyne, and 1-dodecyne, the alkynols propargyl alcohol, 1-butyn-3-ol, 2-butyn-1-ol, 2-butyne-1,4-diol, 1-pentyn-3-ol, 2-pentyn-1-ol, 4-pentyn-1-ol, 4-pentyn-2-ol, 3-hexyn-1-ol, 5-hexyn-1-ol, 3-hexyne-2,5-diol, 2-octyn-1-ol, 1-octyn-3-ol, 3-nonyn-1-ol, 3-decyn-1-ol, or else propargyl chloride, propargyl bromide, propargylamine, propiolic acid, methyl propiolate, ethyl propiolate, 2-butynoic acid, ethyl 2-butynoate, 4-pentynoic acid, 5-hexynonitrile, 2-octynoic acid, methyl 2-octynoate, methyl 2-nonynoate, acetylenedicarboxylic acid, diethyl acetylenedicarboxylate and dimethyl acetylenedicarboxylate.

Preferred alkynes (acetylenes) used comprise the 1-alkynes, propargyl alcohol, butynediol, propiolic acid, and acetylenedicarboxylic acid derivatives.

It is particularly preferable to use ethyne (acetylene) itself.

Familiar oxidants are used to oxidize the resultant phosphonous acid end groups to give phosphonic acid end groups.

Hydrogen peroxide or ammonium peroxodisulfate is preferably used for the oxidation process.

In one particular embodiment of the process, the ammonium peroxodisulfate initiator used brings about some oxidation of the end groups before preparation of the polymer is complete, and oxidation of the end groups is completed after build-up of the chain has ended.

The reaction of the resultant phosphonous acid end groups to give phosphinic acid end groups takes place via reaction with olefins under conditions which are the same as those described for the reaction with alkynes.

The olefins used preferably comprise ethylene, propylene, n-butene, isobutene, n-pentene, isopentene, n-hexene, isohexene, n-octene, isooctene, 1-decene, 1,5-cyclooctadiene, 1,3-cyclopentadiene, dicyclopentadiene and/or a mixture of 2,4,4-trimethylpentene isomers.

The olefins preferably bear a functional group.

Other suitable olefins are compounds of the formula

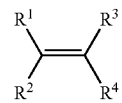

where $R^1$ to $R^4$ may be identical or different, and are hydrogen, an alkyl group having from 1 to 18 carbon atoms, phenyl, benzyl, or alkyl-substituted aromatic systems.

Cycloolefins of the formula

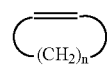

are also suitable, in particular cyclopentene, cyclohexene, cyclooctene, and cyclodecene.

The reaction with olefins preferably takes place after the reaction with alkynes.

The olefin is preferably added before the reaction with alkynes is complete.

Finally, the invention also provides the use of the inventive polymeric phosphinic acids and their salts as flame retardants.

The polymeric phosphinic acids and their salts are preferably used as flame retardants in thermoplastic or thermoset polymers, or else in fire-protection coatings.

The structure of the inventive and novel polymeric phosphinic acids and of their salts gives them the properties of polyelectrolytes. For example, they may be used as thickeners or as water-absorbent agents.

They may also be used to prepare synthetic units for synthesis in organophosphorus chemistry.

The inventive and novel polymeric phosphinic acids and their salts may be described by the formula (I)

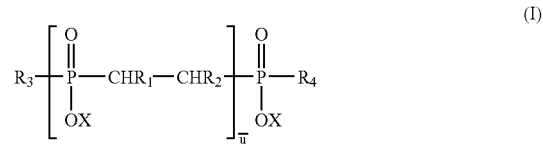

where X is hydrogen or 1/m of a metal of valency m, or is a protonated nitrogen base, $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatic systems, $R_3$ and $R_4$ may be identical or different and are an unsubstituted or substituted alkyl group having from 2 to 20 carbon atoms, or are OX, with the above meaning for X, and $\bar{u}$ is the average number of monomer units. Preferred values for $\bar{u}$ are from 2 to 1 000, but $\bar{u}$ may also, where appropriate, assume larger values.

As is usual in polymer terminology, $\bar{u}$ means the average number of monomer units, and $\bar{u}$ here is calculated from the total number of monomer units per polymer molecule and the distribution (frequency) of the various polymer molecules.

According to the definition below, and on the basis of the reaction scheme described in further detail at a later stage below, u, which in the formula (Ia) given by way of example is analogous to ū and gives the relative number of monomer units, may be any desired number from 0 to 10 000, or else, where appropriate, above 10 000.

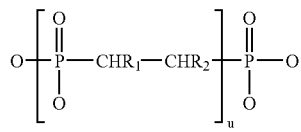
(Ia)

If the value for u=1 in the abovementioned formula (Ia) given by way of example, the result is ethylenediphosphonic acid. Dimers, trimers, etc. may also be obtained in correspondingly fashion.

In the case of polymeric phosphinic acids and their salts where the value is relatively small (e.g. ū=3), it can be said here in relation to the average chain length ū that values of u in the range from 0 to about 6 are more likely to occur, whereas the frequency of medium-size and relatively long polymer chains tends toward zero. On the other hand, if the value of ū is very large (e.g. ū=500), the number of monomers, dimers, trimers, etc. is vanishingly small or zero, while u, i.e. the relative number of monomer units, tends toward relatively large numeric values, in particular here in the range from 350 to 700.

Surprisingly, it has now been found that a wide range of the abovementioned polymeric phosphonic acids and their salts can in particular be prepared in a simple and particularly cost-effective manner via free-radical-initiated polyaddition reaction of alkynes (acetylenes) onto hypophosphorous acid or its salts, and modification of the resultant phosphonous acid end groups.

By way of example, the underlying principle of the polyaddition reaction may be described from the following simplified reaction scheme, taking the example of the reaction of free hypophosphorous acid: in a first stage (1) of the reaction, an addition reaction occurs involving one P—H bond of the hypophosphorous acid and the triple bond of the alkyne (acetylene), with the aid of a free-radical initiator. A vinylphosphonous acid (IV) occurs as an intermediate in this reaction, and, in a second stage (2) of the reaction, under the same reaction conditions, another addition reaction takes place involving the double bond of (IV) and another hypophosphite molecule.

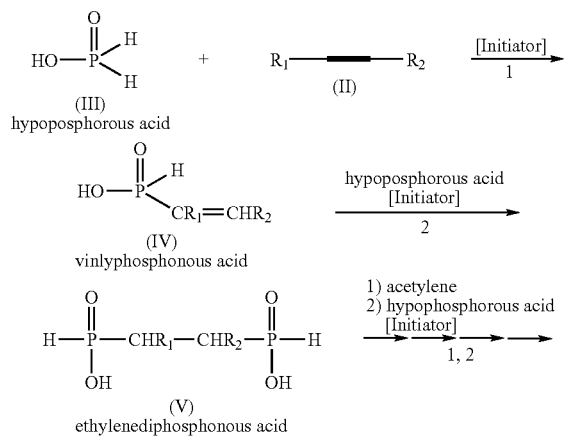

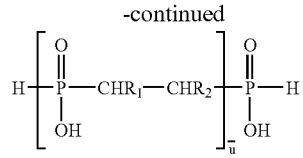
(I; X = H, R₃ = H)
polyethylenephosphinic acid
(phosphonous acid end groups)

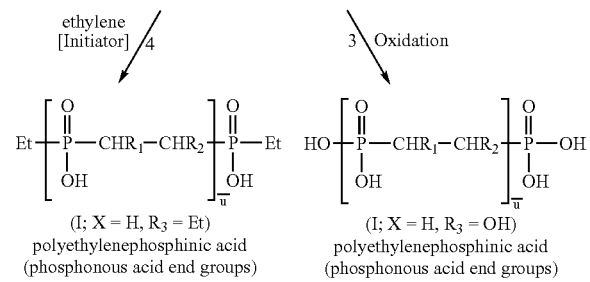

(I; X = H, R₃ = Et)
polyethylenephosphinic acid
(phosphonous acid end groups)

(I; X = H, R₃ = OH)
polyethylenephosphinic acid
(phosphonous acid end groups)

The resultant diphosphonous acid (V) is subjected to an addition reaction onto other acetylene and hypophosphite units, to give polyphosphinic acids (I). The phosphonous acid end groups are then converted into phosphonic acid end groups or phosphinic acid end groups via oxidation (3) or reaction with olefins (in this case ethylene) (4).

The progress of chain build-up may be followed by $^{31}$P NMR spectroscopy during the reaction with alkynes. The integral of the phosphonous acids signal group at δ=about 30 ppm ($int_{phosphonous\ acid}$) represents the end groups present here, while the integral of the phosphonic acids signal group at δ=about 55 ppm ($int_{phosphinic\ acid}$) represents the number of non-terminal groups. The chain length calculation follows the following formula:

$$\bar{u} = 1 + \frac{2\,int_{phosphinic\ acid}}{int_{phosphonous\ acid}}$$

The chain length of the end products obtained after modification can also be assessed by this formula, but the signal group for the phosphinic acid end groups or for the phosphonic acid groups has to be used in the formula instead of the integral of the phosphonous acid signal group.

The chain length of the novel polyphosphinic acids and their salts may be controlled in a simple manner and varied to a high degree via the selection of the reaction conditions. The most important control factor here is the ratio of the starting materials. By way of example, if equimolar amounts of hypophosphite and ethyne (acetylene) are used and high reaction times and high reaction temperatures are applied, the result is particularly high-molecular-weight polyphosphinic acids, where ū>100.

If, by way of example, the molar ratio of starting materials used is 1 (hypophosphite) to 0.75 (acetylene), the result is a particularly low-molecular-weight polyphosphinic acid having an average chain length of ū=3.

In the case of gaseous alkynes (acetylenes), such as ethyne (acetylene), the parent compound itself, the reaction can be controlled via the gas supply time. Greater duration of ethyne (acetylene) supply results in build-up of longer chains.

In the present invention, two hypophosphite radicals undergo a stepwise addition reaction onto the triple bond, described in formula (1), preferably in the 1,2-position. Depending on the steric and electronic effects of the substituents ($R_1$ and $R_2$) in the alkyne (acetylene) used, a 1,1-addition reaction may also take place, and therefore the polymeric phosphinic acids may also have structural units of the following type, where $R_1$ and $R_2$ and X have the meaning specified at the outset:

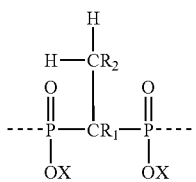

The present invention also provides polymeric phosphinic acids and their salts which contain these structural units.

Especially if the reaction is carried out in dilute solution, cyclopolyaddition can also generate cyclopolyphosphinic acids or their salts of the formula (IX) as by-products

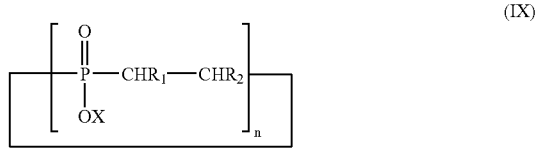

where X is a hydrogen atom or 1/m of a metal of valency m, $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatic systems, and where n is a number from 2 to 100.

The present invention also provides these cyclopolyphosphinic acids and their salts of the formula (IX).

The inventive polymeric phosphinic acids and their properties may be varied not only with respect to their predominant end group but also in many different ways via the selection of the reaction conditions and especially via the selection of the reaction partners.

EXAMPLE 1

Polyethylenephosphinic Acid (Phosphonic Acid End Groups)

At a temperature of about 100° C., gaseous ethyne (acetylene) is passed for a period of 15 h into a solution of 106 g of sodium hypophosphite (1 mol) in 300 ml of glacial acetic acid in a heatable glass tubular reactor with gas-inlet frit. Over the entire period here, a solution of 10.8 g (4 mol %) of 2,2'-azobis(2-amidinopropane)dihydrochloride in 100 g of a water/acetic acid mixture (1:1) is metered uniformly into the mixture. After further reaction has taken place for 0.5 h, and the ethyne (acetylene) has been removed by passing nitrogen through the mixture, 150 ml of 35% strength hydrogen peroxide solution is metered into the mixture within a period of 60 min. After cooling to room temperature, the reaction mixture was freed from the solvents, taken up in 800 ml of water, and treated with 100 g of concentrated hydrochloric acid. The resultant precipitate was filtered, washed twice, each time with 200 ml of water, and dried at 130° C. in the vacuum generated by a water pump. This gave 80 g of a white powder, corresponding to a yield of 76.3%, based on hypophosphite used.

The following signals were found in the $^{31}$P NMR spectrum (NaOD):
- δ from 42 to 48 ppm: broad multiplet (polymeric phosphinic acid groups): integral: 94.5
- δ from 22 to 23 ppm: broad multiplet (phosphonic acid end groups): integral: 3.7, calculated average chain length: $\bar{u}$=52.

EXAMPLE 2

Polyethylenephosphinic Acid (Phosphonic Acid End Groups)

At a temperature of about 105° C., gaseous ethyne (acetylene) is passed for a period of 8 h into a solution of 212 g of sodium hypophosphite (2 mol) in 600 g of glacial acetic acid in a heatable glass tubular reactor with gas-inlet frit. Over the entire period here, a solution of 22.8 g (5 mol %) of ammonium peroxodisulfate in 100 g of a water/acetic acid mixture (1:1) is metered uniformly into the mixture. After further reaction for a period of 0.5 h, and removal of the ethyne (acetylene) by passing nitrogen through the mixture, the reaction mixture was freed from the solvents, taken up in 2 000 ml of water, and treated with 210 g of concentrated hydrochloric acid within a period of 30 min. The resultant precipitate was filtered, washed twice, each time with 500 ml of water, and dried at 130° C. in the vacuum generated by a water pump. This gave 180 g of a white powder, corresponding to a yield of 76.3%, based on hypophosphite used.

The following signals were found in the $^{31}$P NMR spectrum (NaOD):
- δ from 42 to 48 ppm: broad multiplet (polymeric phosphinic acid groups): integral: 92
- δ from 22 to 23 ppm: broad multiplet (phosphonic acid end groups): integral: 3.0, calculated average chain length: $\bar{u}$=62.

EXAMPLE 3

Sodium Salt of Polyethylenephosphinic Acid (Phosphinic Acid End Groups)

At a temperature of about 100° C., gaseous ethyne (acetylene) is passed for a period of 7 h into a solution of 106 g of sodium hypophosphite (1 mol) in 300 ml of glacial acetic acid in a heatable glass tubular reactor with gas-inlet frit. Over the entire period here, a solution of 5.4 g (2 mol %) of 2,2'-azobis(2-amidinopropane)dihydrochloride in 100 g of a water/acetic acid mixture (1:3) is metered uniformly into the mixture. After further reaction for a period of 0.5 h, and removal of the ethyne (acetylene) by passing nitrogen through the mixture, ethylene was passed at 100° C. into the reaction mixture for a further period of 15 h. During this period, a solution of 10.8 g (4 mol %) of 2,2'-azobis(2-amidinopropane)dihydrochloride in 200 g of a water/acetic acid mixture (1:3) was metered uniformly into the mixture. After cooling to room temperature, this gave 660 g of a solution of the sodium salt of the polyethylenephosphinic acid, which was subjected to $^{31}$P NMR spectroscopy.

The signals found here were as follows:

δ from 46 to 50 ppm: broad multiplet (polymeric phosphinic acid groups): integral: 55

δ from 53 to 55 ppm: broad multiplet (phosphonic acid end groups): integral: 34.6, calculated average chain length: $\bar{u}=4.2$.

EXAMPLE 4

Polyethylenephosphinic Acid (Phosphinic Acid End Groups)

At a temperature of about 100° C., gaseous ethyne (acetylene) is passed for a period of 20 h into a solution of 106 g of sodium hypophosphite (1 mol) in 300 g of glacial acetic acid in a heatable glass tubular reactor with gas-inlet frit. Over the entire period here, a solution of 16.2 g (6 mol %) of 2,2'-azobis(2-amidinopropane)dihydrochloride in 100 g of a water/acetic acid mixture (1:3) is metered uniformly into the mixture. After further reaction for 0.5 h, and removal of the ethyne (acetylene) by passing nitrogen through the mixture, ethylene was passed into the reaction mixture at 100° C. for a further period of 15 h. During this period, a solution of 10.8 g (4 mol %) of 2,2'-azobis(2-amidinopropane)dihydrochloride in 200 g of a water/acetic acid mixture (1:3) was metered uniformly into the mixture. After cooling to room temperature, the reaction mixture was freed from the solvents, taken up in 800 ml of water, and treated with 100 g of concentrated hydrochloric acid. The resultant precipitate was filtered, washed twice, each time with 200 ml of water, and dried at 130° C. in the vacuum generated by a water pump. This gave 82 g of a white powder, corresponding to a yield of 77.5%, based on hypophosphite used.

The following signals were found in the $^{31}$P NMR spectrum (NaOD):

δ from 45 to 50 ppm: broad multiplet (polymeric phosphinic acid groups): integral: 89

δ from 53 to 55 ppm: broad multiplet (phosphonic acid end groups): integral: 5, calculated average chain length: $\bar{u}=36.6$.

EXAMPLE 5

Aluminum Salt of Polyethylenephosphinic Acid (Phosphinic Acid End Groups)

330 g (0.5 mol) of the solution obtained as in example 3 and comprising the sodium salt of the polyethylenephosphinic acid were treated with a further 400 g of acetic acid and 13 g (0.166 mol) of aluminum hydroxide, and heated for 6 h at reflux. The mixture was then filtered, and the precipitate was washed twice with water, each time using 300 ml, and the solid was dried at 130° C. in the vacuum generated by a water pump. This gave 36 g of the aluminum salt of polyethylenephsophinic acid, corresponding to a yield of 72%.

The following signals were found in the $^{31}$P NMR spectrum (NaOD):

δ from 46 to 50 ppm: broad multiplet (non-terminal phosphinic acid groups): integral: 65

δ from 53 to 55 ppm: broad multiplet (phosphinic acid end groups): integral: 24.6, calculated average chain length: $\bar{u}=6.3$

EXAMPLE 6

Aluminum Salt of Polyethylenephosphinic Acid (Phosphinic Acid End Groups)

41 g (0.4 mol) of the polyethylenephosphinic acid obtained as in example 4 were slowly introduced into a solution of 16 g (0.4 mol) of NaOH in 100 ml of water, giving a clear solution of the sodium salt of polyethylenephosphinic acid. A solution of 43 g (0.065 mol) of $Al_2(SO_4)_3$ 18 $H_2O$ in 50 ml of water was then added dropwise. The spontaneously precipitating salt was filtered off and washed twice with water, each time using 100 ml. Drying at 130° C. in the vacuum generated by a water pump gave 43.8 g of the aluminum salt of polyethylenephosphinic acid, corresponding to a yield of 96%.

EXAMPLE 7

Melamine Salt of Polyethylenephosphinic Acid (Phosphonic Acid End Groups)

90 g of the polyethylenephosphinic acid obtained as in example 2 were introduced into a solution of 38.7 g of NaOH in 4 000 ml of water, giving a clear solution of the sodium salt of polyethylenephosphinic acid. 157 g of melamine hydrochloride were then introduced in portions at 60° C. within a period of 90 min, and further reaction was permitted for 30 min. The precipitated salt was filtered off and washed twice with water, each time using 1 000 ml. Drying at 130° C. in the vacuum generated by a water pump gave 199 g of melamine salt of polyethylenephosphinic acid, corresponding to a yield of 94%.

What is claimed is:

1. A polymeric phosphinic acid or its salt of the formula (I)

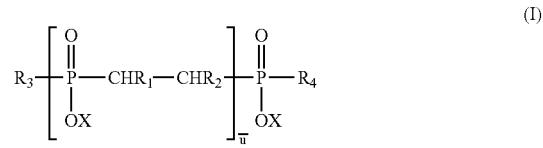

where
X is 1/m of a metal of valency m,
$R_1$ and $R_2$ are identical or different and are hydrogen, a carboxy group, a carboxylic acid derivative, an unsubstituted or substituted alkyl group having from 1 to 10 carbon atoms, phenyl, benzyl, or alkyl-substituted aromatic systems,
$R_3$ and $R_4$ may be identical or different and are an unsubstituted or substituted alkyl group having from 2 to 20 carbon atoms, an OH group or are OX, with the above meaning for X, and
$\bar{u}$ is from 2 to 1000, and wherein X is a metal of groups IIA, IIIA, IVA, VA, IIB, IVB, VIIB, VIIIB of the Periodic Table of the Elements, or is cerium.

2. The polymeric phosphinic acid or its salt as claimed in claim 1, wherein the metal is Mg, Ca, Sr, Ba, Al, Ge, Sn, Sb, Bi, Zn, Ti, Zr, Mn, Fe or Ce.

3. The polymeric phosphinic acid or its salt as claimed in claim 1, wherein the metal is Ca, Al or Zn.

4. The polymeric phosphinic acid or its salt as claimed in claim 1, wherein $R_1$ and $R_2$ are identical or different and are hydrogen or an unsubstituted or substituted alkyl group having from 1 to 10 carbon atoms.

5. The polymeric phosphinic acid or its salt as claimed in claim 1, wherein $R_1$ and $R_2$ are identical or different and are hydrogen, an unsubstituted alkyl group having from 1 to 10 carbon atoms, or a substituted alkyl group having 1 to 10 carbon atoms substituted by OH, CN, or $NH_2$.

6. The polymeric phosphinic acid or its salt as claimed in claim 1, wherein $R_1$ and $R_2$ are identical or different and are hydrogen or an alkyl group having from 1 to 4 carbon atoms which has substitution by one or two OH groups.

7. The polymeric phosphinic acid or its salt as claimed in claim 1, wherein $R_1$ and $R_2$ are identical or different and are hydrogen or a carboxylic acid derivative.

8. The polymeric phosphinic acid or its salt as claimed in claim 1, wherein $R_1$ and $R_2$ are identical or different and are hydrogen or a carboxylic acid derivative of the formula COOR, where R is an alkyl group having from 1 to 4 carbon atoms.

9. The polymeric phosphinic acid or its salt as claimed in claim 1, wherein $R_3$ and $R_4$ are an unsubstituted or substituted alkyl group having from 1 to 10 carbon atoms.

10. The polymeric phosphinic acid or its salt as claimed in claim 1, wherein each of $R_3$ and $R_4$ is an ethyl, propyl or butyl group.

11. The polymeric phosphinic acid or its salt as claimed in claim 1, wherein each of $R_3$ and $R_4$ is an OX group, wherein X is as defined in claim 1.

12. The polymeric phosphinic acid or its salt as claimed in claim 1, wherein each of $R_3$ and $R_4$ is an OH group.

13. A polymeric phosphinic acid or its salt of the formula

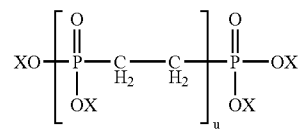

where X=1/m metal of valency m, or amine-$H^+$
and wherein $\bar{u}$ is from 2 to 1000.

14. A polymeric phosphinic acid or its salt of the formula

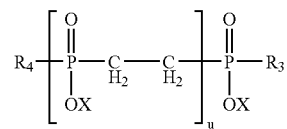

where X=1/m metal of valency m
where $R_3$ and $R_4$=ethyl, propyl, or butyl
wherein X is a metal of groups IIA, IIIA, IVA, VA, IIB, IVB, VIIB, VIIIB of the Periodic Table of the Elements, or is cerium and
$\bar{u}$ is from 2 to 1000.

* * * * *